United States Patent [19]
Holt et al.

[11] Patent Number: 5,942,439
[45] Date of Patent: Aug. 24, 1999

[54] METHOD FOR ISOTOPIC ANALYSIS OF CHLORINATED ORGANIC COMPOUNDS

[75] Inventors: Ben D. Holt, Hindsdale; Neil C. Sturchio, Oswego, both of Ill.

[73] Assignee: The United States of America as represented by the United States Department of Energy, Washington, D.C.

[21] Appl. No.: 08/919,693

[22] Filed: Aug. 28, 1997

[51] Int. Cl.[6] .............................. G01N 33/00; G01N 1/22
[52] U.S. Cl. ........................ 436/124; 436/126; 436/173; 436/174; 436/181; 436/183; 436/155; 436/158; 436/177
[58] Field of Search ..................................... 436/124, 125, 436/126, 155, 158, 159, 173, 174, 177, 181, 183

[56] References Cited

PUBLICATIONS

"Method for the Conversion of Chlorinated Volatile Organic Compounds to Carbon Dioxide and Methyl Chloride for Isotopic Analysis of Carbon and Chlorine" American Chemical Society National Meeting, Aug. 29, 1996—Ben D. Holt, et al.

"High Temperature Method for Conversion of Chlorinated Organic Compounds to CH3Cl and C02 for Isotopic Analysis of Chlorine and Carbon", Holt, et. al, Abstracts of Papers of the American Chemical Society, v.212, pp. 154, Published Aug. , 29, 1996.

"Conversion of Chlorinated Organic Compounds to Carbon Dioxide and Methyl Chloride for Isotopic Analysis of Carbon and Clorine" Holt, et al, Analytical Chemistry, v.69, pp. 2727–2733. Published Oct. 15, 1997.

*Primary Examiner*—Arlen Soderquist
*Assistant Examiner*—Kevin P. Cannell
*Attorney, Agent, or Firm*—Joy Alwan; Thomas G. Anderson; William R. Moser

[57] ABSTRACT

The present invention provides a method for preparing a VOC sample for carbon and chlorine isotope ratio analysis by mass spectrometer. A VOC sample is placed in a combustion tube and reacted with CuO to form $CO_2$ and CuCl. The $CO_2$ is then extracted and analyzed for the carbon isotope ratio. The CuCl is separated from the excess CuO and reacted with $CH_3I$ to form $CH_3Cl$, extracted and analyzed for chlorine isotope ratio.

19 Claims, 8 Drawing Sheets

Yields and $\delta^{37}Cl$ values for $CH_3Cl$ (from $CuCl + CH_3I$) reaction under various experimental conditions.

| Experimental Conditions | Replicates (n) | Yield (%) | Replicates (n)* | $\delta^{37}Cl$ |
|---|---|---|---|---|
| CuCl unheated | 5 | 99±1 | 2 | 2.1±0.1 |
| CuCl evaporated | 4 | 98±1 | 1 | 1.9 |
| CuCl heated with CuO (550°); evaporated | 9 | 90±4 | 3 | 1.8±0.1 |
| 0.5μL $H_2O$ added; CuCl heated (550°); no CuO; evaporated | 6 | 85±8 | 5 | 2.2±0.2 |

*partial set of samples from yield test

FIG. 5

Yields and $\delta^{37}Cl$ offsets for $CH_3Cl$ samples using different CuCl evaporation

| Conditions for re-evaporation of CuCl | Replicates (n) | CO$_2$ | | CH$_3$Cl | |
|---|---|---|---|---|---|
| | | Yield (%) | $\delta^{13}Cl$ (‰) | Yield (%)* | $\Delta^{37}Cl$ (‰) |
| Vertical tube-furnace @ 790 °C CuO flame-heated @ glass m.p. | 5 | 100±1 | −58.02±0.08 | 87±1 | −0.45±0.03 |
| Horizontal tube furnace @ 700 °C CuO not flame-heated | 6 | 99±1 | nm | 89±1 | −0.23±0.05 |
| Horizontal tube furnace @ 595 °C CuO not flame-heated | 2 | 99±1 | nm | 92±1 | −0.26±0.01 |

*uncorrected Cl yield
$\Delta^{37}Cl = \delta^{37}Cl$ product $- \delta^{37}Cl$ orginal
nm = not measured

FIG. 6

Yields and isotopic data for duplicate analyses of various chlorinated compounds

| Compound | CO$_2$ Yield (%) | CO$_2$ $\delta^{13}$C (‰) | CH$_3$Cl Yield* (%) | CH$_3$Cl $\delta^{37}$C (‰) |
|---|---|---|---|---|
| CH$_3$Cl | 99 | −58.77 | 93 | −0.25 |
|  | 98 | −58.03 | 91 | −0.26 |
| CH$_2$Cl$_2$ | nm | −34.17 | 91 | +1.56 |
|  | nm | −34.21 | 91 | +1.55 |
| CHCl$_3$ | nm | −43.25 | 90 | −1.51 |
|  | nm | −43.17 | 89 | −1.53 |
| CCl$_4$ | 100 | −47.18 | 91 | −0.02 |
|  | 100 | −47.25 | 92 | −0.01 |
| C$_2$H$_2$Cl$_2$ | nm | −27.34 | 88 | +0.35 |
|  | nm | −27.37 | 88 | +0.51 |
| C$_2$HCl$_3$ | nm | −27.17 | 91 | −1.32 |
|  | nm | −27.19 | 88 | −1.51 |
| C$_2$Cl$_4$ | nm | −24.06 | 89 | +0.49 |
|  | nm | −24.09 | 88 | +0.56 |
| C$_2$H$_3$Cl$_3$** | nm | −25.49 | 80 | −2.86 |
|  | nm | −25.58 | 79 | −2.87 |
| CuCl | na | na | 99 | +2.13 |
|  | na | na | 98 | +2.10 |
| CuCl$_2$*H$_2$O | na | na | 95 | +0.44 |
|  | na | na | 97 | +0.40 | nm = not measured
na = not applicable
*uncorrected Cl yield
**solvent grade, containing 5% "preservative"

METHOD FOR ISOTOPIC ANALYSIS OF CHLORINATED ORGANIC COMPOUNDS

CONTRACTUAL ORIGIN OF THE INVENTION

The United States Government has rights in this invention pursuant to Contract Number W-31-109-ENG-38 between the U.S. Department of Energy and the University of Chicago representing Argonne National Laboratory

BACKGROUND OF THE INVENTION

1. Field of the Invention

The present invention relates to a method for detecting and tracing volatile chlorinated organic compounds primarily as ground water contaminants. The invention provides a method for reacting a volatile chlorinated organic compound with CuO to form $CO_2$ and CuCl and then reacting the CuCl with $CH_3I$ to form $CH_3Cl$. The $CO_2$ and $CH_3Cl$ are then subjected to mass spectrometric isotope ratio analysis.

2. Background of the Invention

Chlorinated volatile organic compounds (VOCs), including the common solvents perchloroethylene, trichloroethylene, trichloroethane, and carbon tetrachloride, are among the most frequently detected groundwater contaminants in the United States. These compounds are known or suspected to be carcinogenic or mutagenic in humans. They are readily transported by groundwater, and are not reduced to acceptable concentrations for human consumption by most municipal water supply treatments; thus they represent a significant hazard to a large portion of the human population.

Measurements of the stable carbon and chlorine isotope ratios of chlorinated VOCs could be useful in tracing sources of these compounds and their breakdown products in the environment. This is particularly the case if these compounds have varied isotope ratios as a result of their manufacture and if biodegradation induces significant isotopic fractionation between residual reactants and products. It is currently difficult to determine the efficiency of natural attenuation or engineered bioremediation as a means of restoring soils and aquifers contaminated with chlorinated VOCs, but the possibility of using isotopic ratios to trace this process is now being explored. Some work has been done on measurement of stable chlorine isotopes in natural waters and rocks and recent work has been reported on a few selected chlorinated organic solvents.

Currently used analytical methods require that $CO_2$ and $CH_3Cl$ be prepared from a chlorinated compound by separate procedures. Van Warmerdam et al. prepared $CO_2$ by combusting samples of some chlorinated solvents with CuO at 550° C. by a published method. They then obtained $CH_3Cl$ on separate samples of each solvent by first combusting in a Parr bomb (ASTM method D808-91) to produce chloride in carbonate solution (with yields in the range of 65–75%), and then converting the chloride to $CH_3Cl$, by a commonly used method of reacting AgCl with $CH_3I$. According to this method, the inorganic chloride is precipitated as AgCl, which is washed, filtered and dried before being sealed in a reaction tube with excess $CH_3I$ and heated for two days at 110–125° C. for reaction. The resulting $CH_3Cl$ is separated from the $CH_3I$ by gas chromatography before mass spectrometric determination of $^{37}Cl/^{35}Cl$. Other methods of converting chlorinated VOCs to inorganic chloride for conversion to $CH_3Cl$ involve reaction with sodium metal or lithium metal.

SUMMARY OF THE INVENTION

It is an object of the present invention to produce $CO_2$ and $CH_3Cl$ from the same sample of chlorinated volatile organic material in the same reaction tube for isotopic ratio studies.

It is an object of the present invention to produce a high yield of both $CO_2$ and $CH_3Cl$ with no aqueous precipitation step.

It is an object of the present invention to produce $CO_2$ and $CH_3Cl$ suitable for mass spectrometric isotope ratio analysis without the need for further purification.

Briefly, the invention provides a method for preparing volatile chlorinated organic compounds for mass spectrometric isotope ratio analysis by first reacting the VOC with CuO to form $CO_2$ and extracting the $CO_2$ for isotope ratio analysis. Then the CuCl formed during the reaction is separated from the excess CuO and reacted with wh $CH_3I$ to form $CH_3Cl$ that is also subjected to isotope ratio analysis.

BRIEF DESCRIPTION OF THE DRAWINGS

These and other objects and advantages of the present invention will become readily apparent upon consideration of the following detailed description and attached drawings, wherein:

FIG. 5 is a table of yields and $^{37}Cl$ values.

FIG. 6 is a table of yields and $^{37}Cl$ values for different CuCl evaporation procedures.

FIG. 7 is a table of yields and isotopic data for duplicate analysis of various chlorinated compounds.

DETAILED DESCRIPTION OF THE INVENTION

The present invention provides a method for preparing a VOC sample for carbon and chlorine isotope ratio analysis by mass spectrometer. A VOC sample is placed in a combustion tube and reacted with CuO to form $CO_2$ and CuCl. The $CO_2$ is then extracted and analyzed for the carbon isotope ratio. The CuCl is separated from the excess CuO and reacted with $CH_3I$ to form $CH_3Cl$, extracted and analyzed for chlorine isotope ratio.

Figure 4:
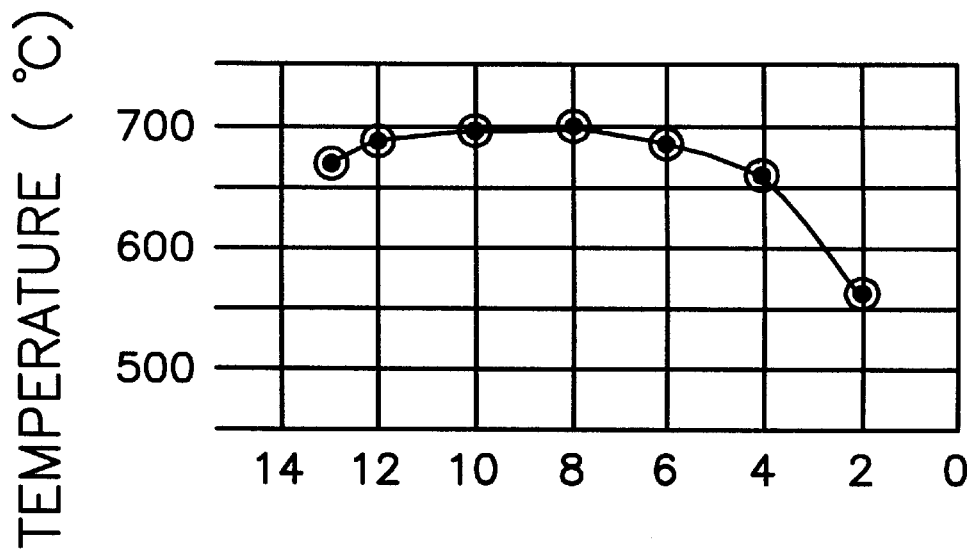
FIG. 4 is a temperature versus time graph for the furnace.
Figure 1:
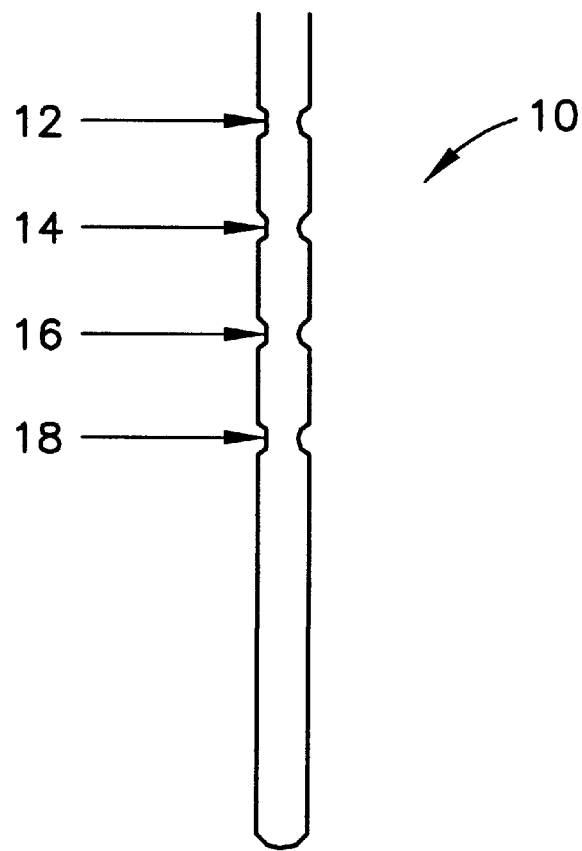
FIG. 1 is a longitudinal cut away view of the combustion tube.

FIG. 1 shows the combustion tube 10. The combustion tube is a 20 cm, 9 mm o.d. borosilicate glass having four 7 mm o.d. constrictions. Constrictions 12 and 16 are for sealing the combustion tube and constrictions 14 and 18 are for cracking open the tube. 1 g of CuO (wire form, 240 $\mu$ sieve) is placed in the combustion tube 10. The tube is then ignited at 550° C. for approximately 2 hours in furnace 92 to ensure that any carbonaceous contamination is removed. After ignition, the tube is attached to the reaction apparatus 20.

Figure 2:
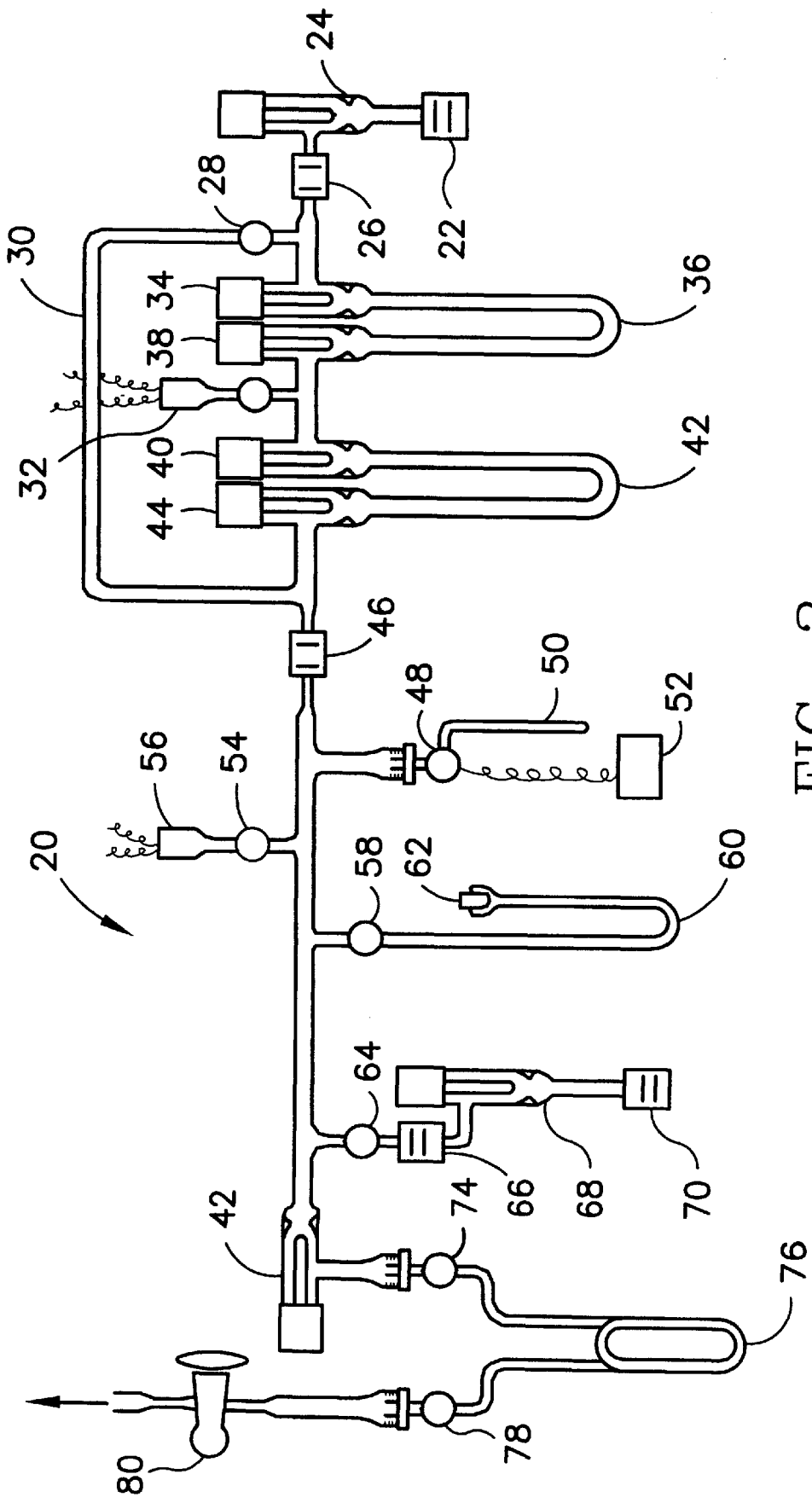
FIG. 2 is a schematic representation of the reaction apparatus used to produce $CO_2$ and $CH_3Cl$.

FIG. 2 shows the reaction apparatus 20. It is a grease free, all glass vacuum line designed to sample, measure, and encapsulate gas or liquid samples. It is used to purify, measure, and encapsulate $CO_2$ and $CH_3Cl$ for subsequent mass spectrometric analysis. All of the valves are Teflon™. The flexible joints are Cajon™ joints. The reaction apparatus 20 is connected to a main vacuum manifold which is not shown. The main manifold includes a thermocouple gauge, a liquid nitrogen cold trap, an oil diffusion pump, and a mechanical roughing pump.

The combustion tube 10 containing the ignited CuO is attached to the reaction apparatus 20 at flexible joint 70. The sampling valve 68 and valve 64 are opened. The combustion tube and reaction apparatus is evacuated. The combustion tube is flamed to remove any absorbed air and moisture. A sample for analysis is injected through septum 62 into the dosing tube 60. Typical samples sizes are 1 to 100 micro moles of a volatile chlorinated organic compound separated from groundwater. Valve 58 is already in the open position. The sample is cryogenically transferred to the combustion tube 10. The tube is sealed at constriction 12 and the CuO is distributed evenly. The combustion tube 10 is heated for 2 hours in furnace 92 of heating 90 at 550° C. The tube is then removed from the furnace and cooled to ambient temperature.

Figure 3:
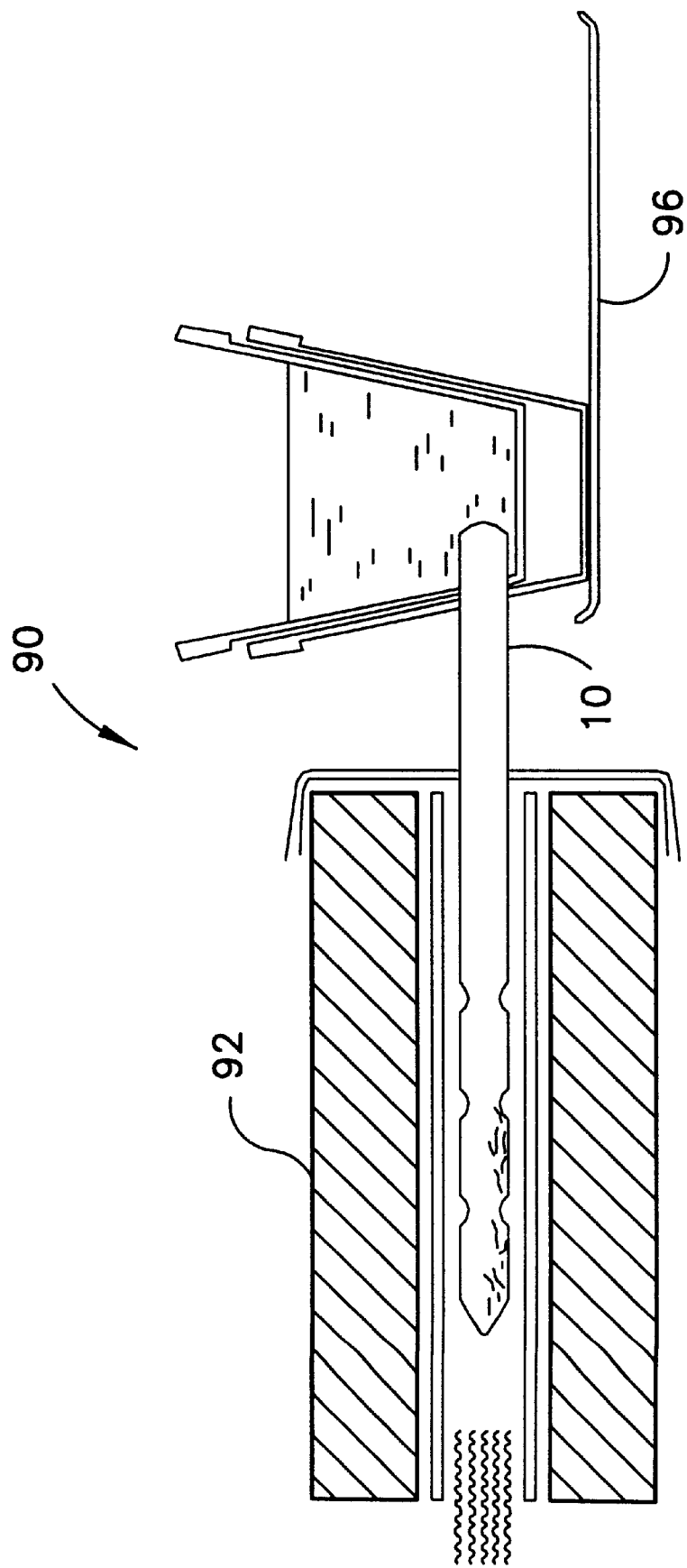
FIG. 3 is a longitudinal cut away view of the furnace and liquid nitrogen cooler.

The CuO is then distributed evenly between constrictions 12 and 16 of the combustion tube 10. The rounded bottom end of the combustion tube is inserted into the snug hole in the side of the liquid nitrogen cooler 94 as shown in FIG. 3. Liquid nitrogen is added to the cooler to condense $CO_2$ and $H_2O$. The cooler 94 is supported on support plate 96. The exposed section of the tube 10 is then inserted into furnace 92 so that constriction 14 is 9 cm from open end of the furnace. After about 45 min of heating at approximately 700° C., the tube is removed and allowed to reach ambient temperature.

After reaching ambient temperature, the tube 10 is positioned so that the remaining CuO is in the constricted end. A large excess of CuO is added initially to ensure that sufficient oxygen is generated to combust all of the VOC. The tube is placed in a tube cracker (not shown) so that the tube will crack at constriction 14. The tube 10 and cracker are attached to the reaction apparatus 20 at valve 24 via flexible joint 22.

A gas sample bulb for collecting the $CO_2$ is attached to sampling valve 68. The sample bulb and reaction apparatus 20 are evacuated. Valves 58, 44, 38, 28 and 24 are closed to prevent sample from transversing bypass line 30. Heat coil 32 is not used after valve 34 is opened. Valve 54 is closed and heat coil 56 is not in use. Cold trap 36 is immersed in an acetone and dry ice slurry and cold trap 42 is immersed in liquid nitrogen. The combustion tube 10 is cracked at constriction 14 and valves 24 and 38 are opened so that $H_2O$ is collected in cold trap 36 and the $CO_2$ is collected in cold trap 42. Valve 44 is opened to pump away any gases not condensed by liquid nitrogen.

The $CO_2$ is transferred from the cold trap 42 to the cold finger 50 through connector 46 and open valve 48 in order to measure the gas pressure. The transfer is made by moving the liquid nitrogen to cold finger 50 and moving the acetone slurry to cold trap 42. Valves 44 and 48 are closed and the gas pressure is measured by an electronic measuring device 52. Valve 72 is closed and the $CO_2$ cryogenically transferred to a glass sample bulb through connector 66. The bulb is sealed and removed from the reaction apparatus 20.

The tube cracker and the combustion tube 10 are removed from the reaction apparatus 20. The portion of the combustion tube holding the CuO is discarded. The remaining portion of the combustion tube contains CuCl condensed on its inner surface. The remaining portion of the combustion tube is reconnected to valve 24. Valves 24, 28, and 72 are then opened to evacuated the combustion tube. The dosing tube 60 is cooled with liquid nitrogen and 35 µl of $CH_3I$ is injected through septum 62. Valve 58 is opened to pump away any air from the injection. Valve 72 is closed and the liquid nitrogen bath is transferred to the combustion tube 10. The dosing tube 60 is heated to transport the $CH_3I$ to the combustion tube.

After the $CH_3I$ is transported to the combustion tube 10, valve 24 is closed and the combustion tube is sealed at constriction 16. Valves 72, 74, 78 and 80 are opened and the reaction apparatus 20 is evacuated through safety loop 76. The combustion tube 10 is heated in a furnace for 2 hours at 300° C. and then cooled to ambient temperature.

The combustion tube is attached to the tube cracker so that it cracks at constriction 18. The tube cracker is attached to the reaction apparatus 20 at valve 24. A glass sample bulb is attached to valve 68. The entire reaction apparatus is evacuated. Valves 58, 44, 38, 28, and 24 are then closed. Cold trap 36 is precooled with liquid nitrogen and then with liquid slush of partially frozen n-pentane. A liquid nitrogen bath is placed around cold trap 42. The combustion tube 10 is cooled in an acetone dry ice slush to enhance the cryogenic separation of $CH_3Cl$ and $CH_3I$.

The combustion tube 10 is cracked at constriction 18. Valves 24 and 38 are opened. After a minute valve 44 is opened to optimize the distillation of the $CH_3Cl$ from the combustion tube through cold trap 36 (~130° C.) to cold trap 42 (~196° C.). After about 10 minutes, the acetone dry ice slush is removed from the combustion tube. After the $CH_3Cl$ has distilled, valves 38, 40, 64, and 72 are closed.

The $CH_3Cl$ is transferred to cold finger 50 to measure the gas pressure. The transfer is made by moving the liquid nitrogen bath from cold trap 42 to the cold finger. The n-pentane slush is transferred from cold trap 36 to cold trap 42 to trap $CH_3I$. After the pressure reading on gauge 56 has dropped, valves 44 and 48 are closed. The pressure is read on an electronic measuring device 52. The $CH_3Cl$ is transferred from the cold finger 50 to the sample bulb attached to the sample valve 68. The sample bulb is then sealed to contain the $CH_3Cl$ for isotopic analysis.

RESULTS AND DISCUSSION

Purities of $CO_2$ and $CH_3Cl$. Mass spectrometric analyses of the $CO_2$ and the $CH_3Cl$ produced by the method typically showed both gases to be >99% pure when the final form of the procedure was followed. Earlier in the development of the method, when the $CO_2$ was cryogenically separated from $H_2O$ by a 1-step application of dry iceacetone, the $CO_2$ product contained 1–2% $H_2O$. The adopted 2-step purification procedure yields $CO_2$ with only traces of impurities. Likewise, in the case of $CH_3Cl$, the 2-step purification procedure, using n-pentane slush to separate $CH_3Cl$ from $CH_3I$, is necessary to reduce the $CH_3I$, content in the product $CH_3Cl$ to ~0.2%. For the sample size range used in this work (10–70 µmol), further purification of the $CH_3Cl$ (e.g., by GC) was not necessary for subsequent mass spectrometric determination of $\delta^{37}Cl$.

Figure 8:
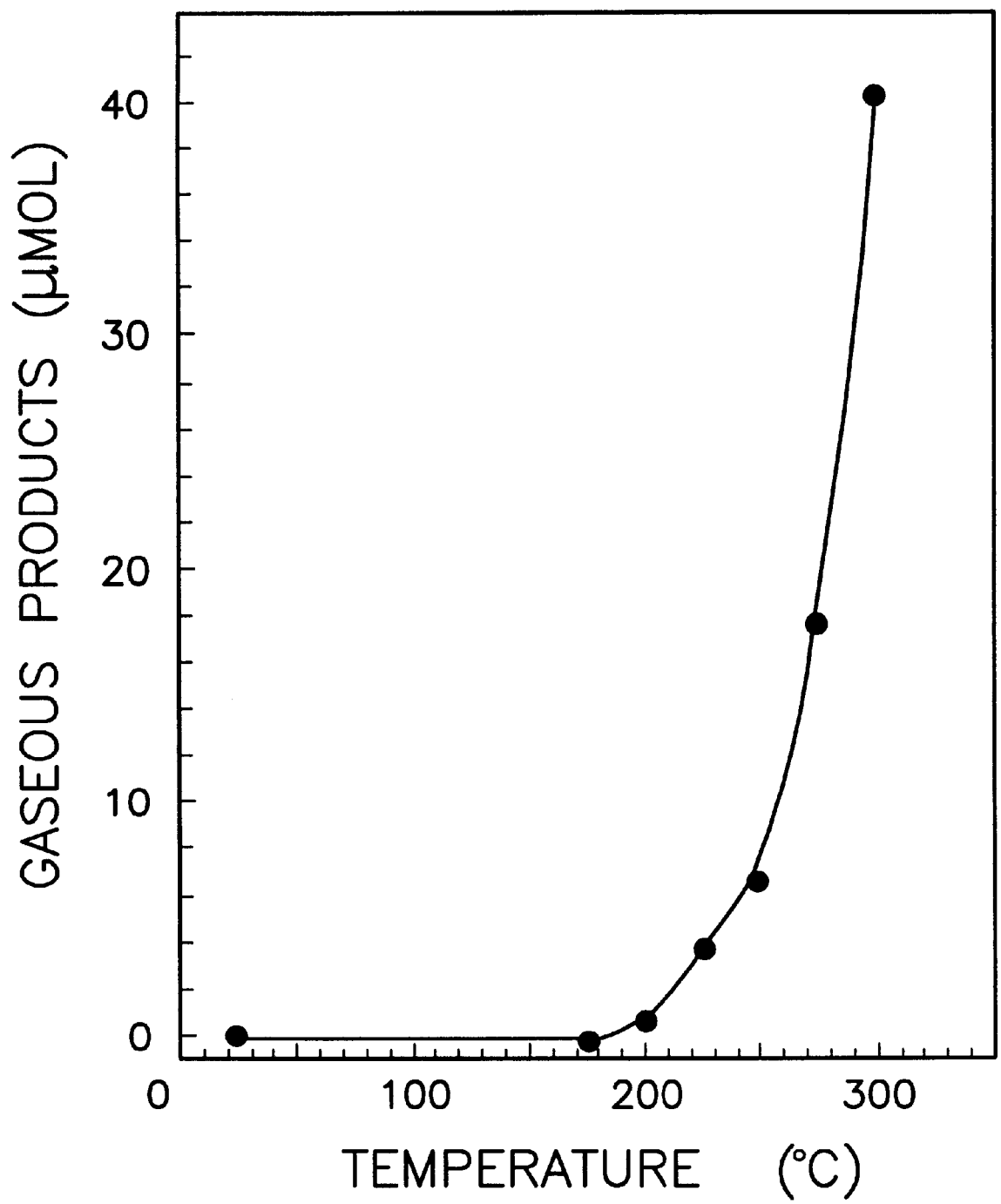
FIG. 8 is a graph of the reactions of $CH_3I$ with CuO showing yields of undesired products.

Separation of the excess CuO from the combustion tube, after the combustion reaction and before the reaction of the newly formed CuCl with $CH_3I$, was essential. If not removed, the CuO reacted with the $CH_3I$ at 300° C. to produce intolerable amounts of gaseous contaminants, such as $CO_2$ and a mixture of unidentified organic products. FIG. 8 shows the effect of heating 35-µl samples of $CH_3I$, each with 1 g of CuO at various temperatures.

Yields of $CO_2$ and $CH_3Cl$. The yields of $CO_2$ from the combustion of a variety of chlorinated organic compounds were typically 99±1%. These results indicate complete oxidation of the organic carbon of the materials. Very few problems were experienced with charring or tube breakage An important precaution for the prevention of charring was to evenly distribute the CuO in the borosilicate combustion tube before placing it horizontally in the furnace at 550° C. Breakage of the glass tubes by thermal shock, after being sealed off by a methane-oxygen torch, was avoided by sealing at the appropriate preformed constriction.

The overall yields of $CH_3Cl$ from a variety of chlorinated organic compounds were typically 89±4%. A search to find the source(s) of the deficiency in complete yield was centered on four phases of the analytical method. A discussion of the apparent effects of each of these four phases on the overall yield of $CH_3Cl$ follows.

Effect of Separation and Purification of the $CH_3Cl$. This phase of the procedure was apparently responsible for ~2% of the deficiency in yield. This is based on a test involving five samples in which amounts of tank $CH_3Cl$ ranging from 9.1 to 69.2 $\mu$mol were each mixed with 35 $\mu$l of $CH_3I$ in sealed tubes and subjected to the procedural steps of separation and purification. The average yield for these five samples was 98±1%. When the condensates in the two cold traps, 36 and 42, were cryogenically returned to the combustion tube and the procedural steps repeated, the yield was 100±1%. For normal use of the method, our preference was to forego a repetition of the purification procedure, and apply a correction factor of 1/0.98 to overall yield data.

One potential cause for poor yields of $CH_3Cl$ in the purification procedure was incomplete cryogenic separation from the excess $CH_3I$ during the transfer from the reaction tube to the manometer. It was important that the mixture be cooled with dry ice-acetone slush (-79° C.) before breaking open the combustion tube for the transfer. This allowed most of the more volatile $CH_3Cl$ to separate from the $CH_3I$ before entering the pentane slush cold trap (-130° C.) where co-condensation with relatively large amounts of $CH_3I$ prolonged the residence time of the $CH_3Cl$ in the trap.

Another potential cause for poor yields of $CH_3Cl$ was failure to allow enough time for the cryogenic transfer from one cold trap to another. These transfers occur at a gas pressure approximating that of the vapor pressure of $CH_3Cl$ at -130° C. This low pressure requires that the inside diameter of the glass line be as large as practical and that adequate time be allowed for complete cryogenic transfer.

The purification procedure separated the $CH_3Cl$ not only from excess $CH_3I$ but also from products of thermal decomposition of small amounts of the $CH_3I$. These thermal decomposition products, from the reaction, $4CH_3I$, $\leftarrow\rightarrow 2CH_4+I_2+CH_2ICH_2I$, were easily identified. The $I_2$ was seen as a violet-colored vapor in the heated reaction tube and as a bronze-colored solution in the excess liquid $CH_3I$ in the cooled reaction tube. The $CH_4$ was collected by a Toepler pump and identified by mass spectrometry. The $CH_2ICH_2I$ was identified as a yellow solid of low vapor pressure on the inner walls of the vacuum line.

Effect of the Reaction of CuCl with $CH_3$ I. The reaction, $CuCl+CH_3I\leftarrow\rightarrow CH_3Cl+CuI$, apparently proceeded to nearly complete yields of $CH_3Cl$ within 2 hours when CuCl was heated with a large excess of $CH_3I$ in a sealed tube at 300° C.

FIG. 5 gives results on 4 sets of samples of a supply of reagent grade CuCl. 75-$\mu$mol samples were weighed out in borosilicate glass capsules (8-mm length×4-mm o.d.) and dropped into the combustion tubes before forming the 7-mm constrictions in the tubes for sealing. The samples of the first set were untreated before the $CH_3I$ reaction. The samples of the second set were not carried through the combustion step but each was carried through the evaporation step before reaction with $CH_3I$. The samples of the third set were subjected to the entire procedure of the method, including combustion for 2 hours at 550° C. and evaporation of the condensed CuCl in the combustion tube before reaction with $CH_3I$. Each of the samples of the fourth set were enclosed with 0.5 $\mu$L $H_2O$ before heating with $CH_3I$. These data show that with no prior treatment (and with a correction factor of 1/0.98 applied for loss in the $CH_3Cl$ purification procedure described above), the average yield of $CH_3Cl$ from the reaction of CuCl with $CH_3I$ was >99%. This is comparable to the best that can be expected from the AgCl—$CH_3I$ reaction step of other methods.

Figure 9:
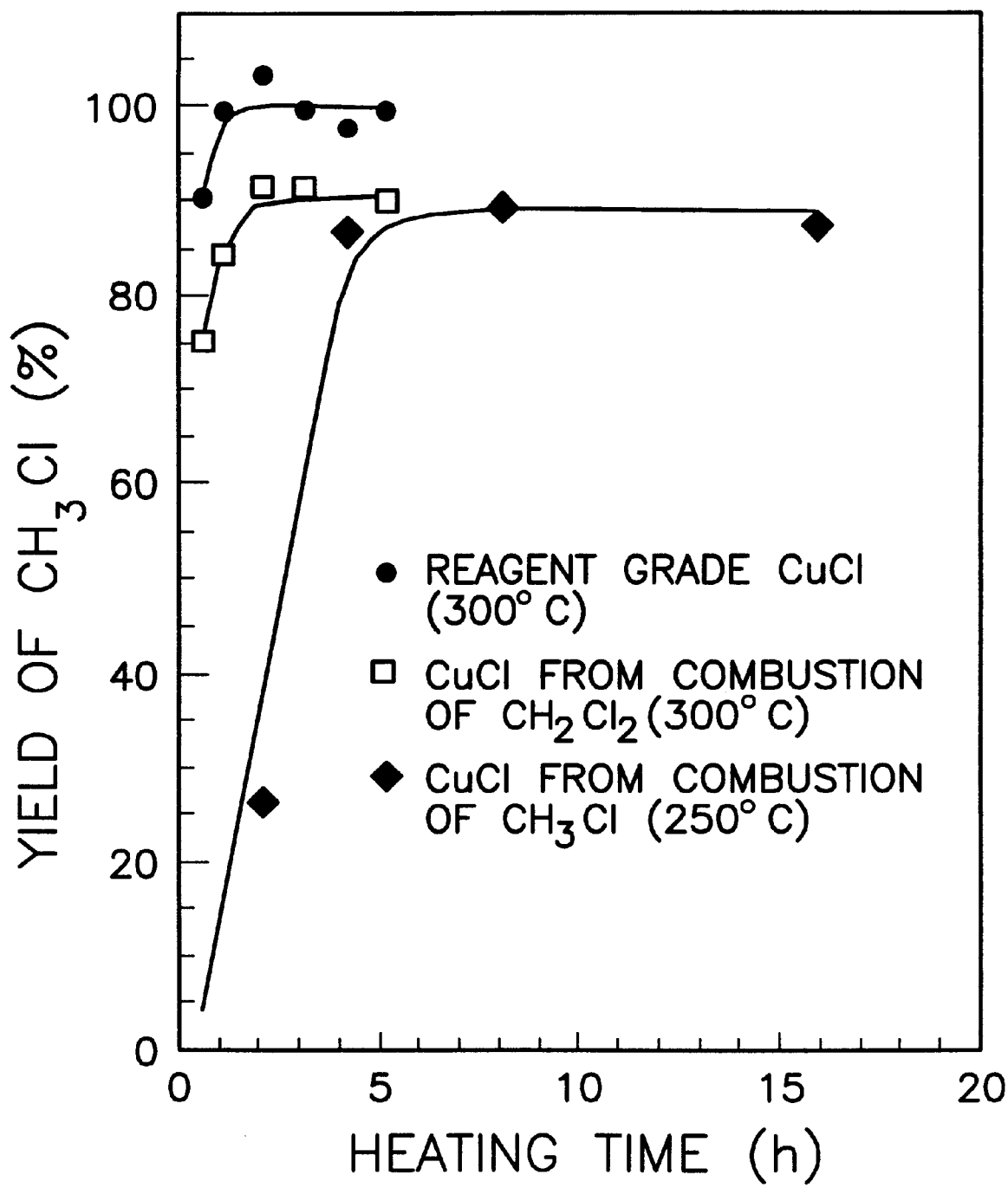
FIG. 9 is a graph of the yield of $CH_3Cl$ versus heating time.

FIG. 9 shows the effects of temperature and the duration of heating on the yield of $CH_3Cl$. The yields of $CH_3Cl$ are plotted vs. heating times for reagent CuCl at 300° C. and for CuCl formed by the combustion of two chlorinated organic compounds at 300° and 250° C. The optimum heating conditions for the reaction were 2 hours at 300° C. Other experiments showed that higher temperatures induced excessive thermal decomposition of the $CH_3Cl$ and lower temperatures required unnecessarily long reaction times. Although the plotted data in FIG. 9 indicate that the reaction at 300° C. was essentially complete within 1 hour, our practice was to heat for 2 hours.

The possibility of interference by $I_2$ in the reaction, $CH_3Cl+I_2\leftarrow\rightarrow CH_3I+ICl$, to significantly affect the yield of $CH_3Cl$ was investigated. In one test, three samples of tank $CH_3Cl$ (~75 $\mu$mol) were each heated with 35 $\mu$l $CH_3I$ for 2 hours at 300° C. No appreciable interference by the $I_2$ was evident in the measured recoveries of the $CH_3Cl$. In another test, the CuCl formed from combustion of tank $CH_3Cl$ was equilibrated with $CH_3I$ at lower temperatures (275°, 250°, and 225° C.) to test for any thermal shift in chemical equilibrium that might produce more or less ICl. No appreciable interference was indicated by the respective yields of $CH_3Cl$.

Effect of Combustion of the Sample. The essentially complete recoveries of $CO_2$ in combustion reactions (discussed above) show that no significant deficiency in yield of $CH_3Cl$ can be attributed to incomplete combustion of the chlorinated organic compounds that were examined.

Effects of Physical and/or Chemical Changes in the CuCl. Since only ~2% of the observed average deficiency of ~11% in the overall yield of $CH_3Cl$ can be attributed to the $CH_3Cl$ purification procedure, and 0% can be attributed to either the combustion reaction or the CuCl—$CH_3I$ reaction, the remaining yield deficiency of ~9% is evidently related to what happens to the CuCl after it is formed in the combustion reaction and before it is consumed by reaction with $CH_3I$.

Suspected sources of the incomplete yields in this phase of the method were: (1) incomplete separation of adsorbed CuCl from the excess CuO before discarding the CuO, (2) incomplete reaction of the CuCl with $CH_3I$ vapor because of a protective coating of newly formed CuI on unreacted CuCl, (3) formation of some $CuCl_2$ with the CuCl, and (4) interaction of the CuCl with associated $H_2O$ to form HCl.

Incomplete separation of adsorbed CuCl from the excess CuO was tested by three modified techniques. One was to heat at ~795° C. for 10 min., using only the tube furnace. Another was to heat the tube with a methane-oxygen torch, in the vicinity of the CuO, to the softening point of the glass tube (~850° C.). And another was to heat even more intensely with the torch (~900° C.) for 5 min., resulting in partial thermal decomposition of the CuO to a sintered, brick-red mass of material (probably mostly $Cu_2O$). Comparative yield and $\delta^{37}Cl$ data are given in FIG. 6 for some of these varied heating conditions. The more intense heating (e.g., at the m.p. of glass) resulted in a small decrease in the average yield for $CH_3Cl$ and a more significant decrease in $\delta^{37}Cl$.

The CuCl that evaporated from the heated end of the combustion tube in the tube furnace tended to accumulate in bands of condensate just outside the furnace. To reduce the possibility that the formation of CuI coatings would significantly retard reaction of $CH_3I$ in deeper layers of CuCl, these deposits were dispersed by reevaporation. The reevaporation brought no improvement in yield, showing that the effects of a protective coating of CuI over unreacted CuCl was not significant.

Formation of $CUCl_2$ by the reaction, $2CuCl + CuO \leftarrow\rightarrow CuCl_2 + Cu_2O$, was also shown to not adversely affect the yield of $CH_3Cl$. In two experiments, using samples of reagent $CuCl_2 \cdot 2H_2O$, the $CuCl_2$ was converted to $CH_3Cl$, by the reaction, $2CuCl_2 + 4CH_3I \leftarrow\rightarrow 4CH_3Cl + 2CuI + I_2$, with yields of 95% and 97%.

Formation of HCl in addition to, and perhaps in equilibrium with, $CH_3Cl$ was probably the major source of the loss in yield of Cl as $CH_3Cl$ in this method. The reaction, $2CuCl + H_2O \leftarrow\rightarrow Cu_2O + 2HCl$ is commonly thought to account for the deterioration of pure CuCl in moist air.[12] A test was made to identify HCl gas that might be pumped away as a non-condensible gas through traps cold trap 36 (−79° C.) and cold trap 42 (−196° C.) and out into the vacuum manifold. Three 65-μmol samples of reagent CuCl were each combined with ~55 μmol of $H_2O$ and sealed in combustion tubes. Two of the tubes were heated 2 hours at 550° C., according to the combustion procedure, but with no CuO present. Each of the three tubes was broken open directly into the inlet of a gas mass spectrometer. The measured concentration of HCl in the water vapor was ~200 ppm. The Cl yields for the two $CuCl + H_2O$ mixtures that were carried through the combustion procedure, and for the unheated mixture of $CuCl + H_2O$, were all ~90%, compared to ~100% for CuCl that was neither heated nor exposed to added $H_2O$.

In FIG. 5, the yield and isotopic data for the fourth set of samples also show the effect of sealing 0.5 μL of $H_2O$ in with ~75 μmol of CuCl and carrying through the heating procedure without CuO. Results of this test indicate that the addition of water to the system, while causing significantly lower and more variable yields, also caused more variable $\delta^{37}Cl$ values.

Isotopic Precision of the Method. The isotopic precision of C and Cl isotope ratio measurements for various chlorinated VOCs analyzed using the new method can be assessed from the data in FIGS. 6 and 7. Specifically, the second row in FIG. 6 shows that the standard deviation for five replicate analyses of $CH_3Cl$ by this method is ±0.05%. The mean and standard deviation of the difference in δ values for duplicate analyses of the chlorinated VOCs listed in FIG. 7 are 0.05±0.03% for $\delta^{13}C$ (n=7) and 0.06±0.07% (n=8) for $\delta^{37}Cl$. We thus estimate that the precision is generally better than ±0.1% for both $\delta^{13}C$ and $\delta^{37}Cl$ in the analysis of the pure compounds.

APPLICATIONS OF THE METHOD

The method should be applicable to a wide range of chlorinated organic compounds. Some of the combustion reactions that were examined in this study are:

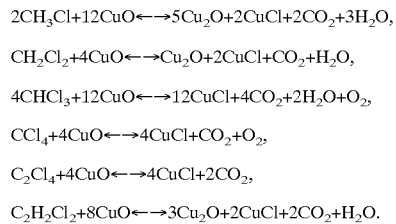

Some of the reaction products were visible on the inner walls of the combustion tube by microscopic examination. The CuCl appeared as finely divided deposits of colorless, solidified droplets. The $Cu_2O$ was visible as sparsely distributed, ruby-red crystals. Expectedly, no red crystals were seen among the combustion products of $CHCl_3$, $CCl_4$, or $C_2Cl_4$; also, deposits of $H_2O$ were visible on the tube walls (when cooled below 0° C.) for all of the above reactions except for $CCl_4$ and $C_2Cl_4$.

Analysis of Tank $CH_3Cl$. Samples of tank $CH_3Cl$ were converted to $CO_2 + CuCl$ and then the CuCl was converted back to $CH_3Cl$ by the procedure of the method to test for C and Cl yields and for alteration of the $\delta^{37}Cl$ value of the $CH_3Cl$ by the procedure. FIG. 6 shows the results obtained for yields and isotopic values for both $CO_2$ and $CH_3Cl$ under different conditions of heating, as previously discussed. Results show that by following the procedure of the method, the average recovery of $CH_3Cl$ was 91±1% (after applying the 1/0.98 correction factor for the $CH_3Cl$ purification step), and the $\delta^{37}Cl$ value was offset by −0.23±0.05%.

Analyses of Other Chlorinated Organics. FIG. 7 lists results obtained on a variety of chlorinated VOCs that may be of interest in studies of such pollutants in soils and groundwaters. The method should be applicable to a wider range of such compounds, following the necessary extraction from environmental samples. The presence of excess water in the sample, however, can degrade the precision of the method, as indicated by the relatively larger standard deviation of $\delta^{37}Cl$ values in the fourth row in FIG. 5. Therefore, separation of water from environmental samples before analysis is important. Modifications of the method for environmental samples and for sub-micromolar sample sizes are now being developed in our laboratory.

The range in $\delta^{13}C$ values of the chlorinated organic compounds shown in FIG. 7 is 34‰, indicating that the initial isotopic ratios of such compounds can be useful for environmental tracing. The corresponding range in $\delta^{37}Cl$ values is only 4.5‰, and though it is much smaller than that of $\delta^{13}C$, it is large relative to the ±0.1‰ precision of the method, indicating that initial Cl isotopic ratios of such compounds can be useful for environmental tracing. Isotopic fractionation caused by biological degradation of such compounds in the environment may extend the range of C and Cl isotopic variation significantly. While this type of fractionation may complicate the use of isotopic ratios for source apportionment, it provides a useful approach for helping to understand the extent of natural attenuation of chlorinated VOCs in contaminated groundwater plumes.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for converting volatile chlorinated organic compounds comprising:

sealing the volatile chlorinated organic compound and CuO in a combustion tube;

reacting the volatile chlorinated organic compound and CuO to form $CO_2$ and CuCl;

extracting $CO_2$;

separating the CuCl and CuO by fracturing the combustion tube;

injecting $CH_3I$ into the combustion tube;

sealing the tube;

reacting the volatile chlorinated organic compound and the $CH_3I$; and extracting the $CH_3Cl$.

2. The method of claim 1 wherein the combustion tube is segmented to isolate reaction products from reactants.

3. The method of claim 1 wherein the reaction products are transferred cryogenically from the combustion tube.

4. The method of claim 3 wherein the reaction products are transferred cryogenically in an evacuated reaction apparatus.

5. The method of claim 3 wherein the reaction products are cryogenically transferred by coolants selected from the group consisting of liquid nitrogen, acetone, dry ice, n-pentane and combinations thereof.

6. The method of claim 1 wherein the reactants are reacted at temperatures selected from the range of 500–700° C.

7. The method of claim 1 wherein the volatile chlorinated organic compound is selected from a size range of 1–100 micro moles.

8. The method of claim 1 wherein the CuO is reacted with the volatile chlorinated organic compound in a combustion tube which is simultaneously heated and cooled.

9. The method of claim 1 wherein the combustion tube and CuO are heated to remove contamination.

10. The method of claim 1 wherein the $CO_2$ is transferred cryogenically to a gas sample bulb.

11. The method of claim 1 wherein the $CH_3Cl$ is transferred cryogenically to a gas sample bulb.

12. A method for converting volatile chlorinated organic compounds to $CO_2$ and $CH_3Cl$ for mass spectrometric isotope ratio analysis comprising:

sealing the volatile chlorinated organic compound and CuO in a combustion tube;

reacting the volatile chlorinated organic compound and CuO to form $CO_2$ and CuCl;

extracting $CO_2$ into a gas sample bulb;

separating the CuCl and CuO by fracturing the combustion tube;

injecting $CH_3I$ into the combustion tube;

sealing the tube;

reacting the volatile chlorinated organic compound and the $CH_3I$ to form $CH_3Cl$;

extracting the $CH_3Cl$ into a gas sample bulb; and analyzing the $CO_2$ and $CH_3Cl$ by mass spectrometric isotope ratio analysis.

13. The method of claim 12 wherein the combustion tube is segmented to isolate reaction products from reactants.

14. The method of claim 12 wherein the reaction products are transferred cryogenically from the combustion tube.

15. The method of claim 14 wherein the reaction products are transferred cryogenically in an evacuated reaction apparatus.

16. The method of claim 14 wherein the reaction products are cryogenically transferred by coolants selected from the group consisting of liquid nitrogen, acetone, dry ice, n-pentane and combinations thereof.

17. The method of claim 12 wherein the reactants are reacted at temperatures selected from the range of 500–700° C.

18. The method of claim 12 wherein the volatile chlorinated organic compound is selected from a size range of 1–100 micro moles.

19. The method of claim 12 wherein the CuO is reacted with the volatile chlorinated organic compound in a combustion tube which is simultaneously heated and cooled.

* * * * *